United States Patent
Sasaki

(10) Patent No.: US 6,718,003 B2
(45) Date of Patent: Apr. 6, 2004

(54) GANTRY OF AN X-RAY COMPUTER TOMOGRAPHY APPARATUS

(75) Inventor: Tomiya Sasaki, Otawara (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/390,299

(22) Filed: Sep. 3, 1999

(65) Prior Publication Data

US 2002/0009174 A1 Jan. 24, 2002

(30) Foreign Application Priority Data

Oct. 16, 1998 (JP) .......................................... 10-295886

(51) Int. Cl.⁷ .............................................. G01N 23/00
(52) U.S. Cl. ................... 378/4; 378/4; 378/19; 378/21; 378/210
(58) Field of Search ............................ 378/4, 19, 199, 378/17, 21, 901, 9, 139, 208, 210

(56) References Cited

U.S. PATENT DOCUMENTS

| | | | | |
|---|---|---|---|---|
| 4,187,429 A | * | 2/1980 | Tomita et al. | |
| 4,366,577 A | * | 12/1982 | Brandt | 378/194 |
| 5,432,339 A | * | 7/1995 | Gordon et al. | 378/4 |
| 5,448,607 A | * | 9/1995 | McKenna | 378/4 |
| 5,448,608 A | * | 9/1995 | Swain et al. | 378/4 |
| 5,448,610 A | * | 9/1995 | Yamamoto et al. | 378/19 |
| 5,473,657 A | * | 12/1995 | McKenna | 378/4 |
| 5,499,415 A | * | 3/1996 | McKenna | 5/601 |
| 5,761,269 A | * | 6/1998 | Sugihara et al. | 378/199 |
| 5,857,007 A | * | 1/1999 | Haq | 378/19 |
| 5,982,843 A | * | 11/1999 | Bailey et al. | 378/4 |
| 5,982,844 A | * | 11/1999 | Tybinkowski et al. | 378/4 |
| 6,031,888 A | * | 2/2000 | Ivan et al. | 378/20 |
| 6,188,743 B1 | * | 2/2001 | Tybinkowski et al. | 378/4 |

* cited by examiner

Primary Examiner—David V. Bruce
Assistant Examiner—Hoon Song
(74) Attorney, Agent, or Firm—Oblon, Spivak, McClelland, Maier & Neustadt, P.C.

(57) ABSTRACT

A gantry of an X-ray computer tomography apparatus comprises a base, two main posts mounted on the base at right angles, a ring frame tiltably supported by the two main posts, a rotation ring rotatably supported by the ring frame, an X-ray tube mounted on the rotation ring, and an X-ray detector mounted on the rotation ring, opposing to the X-ray tube. The props obliquely abut on the main posts to reinforce them.

16 Claims, 5 Drawing Sheets

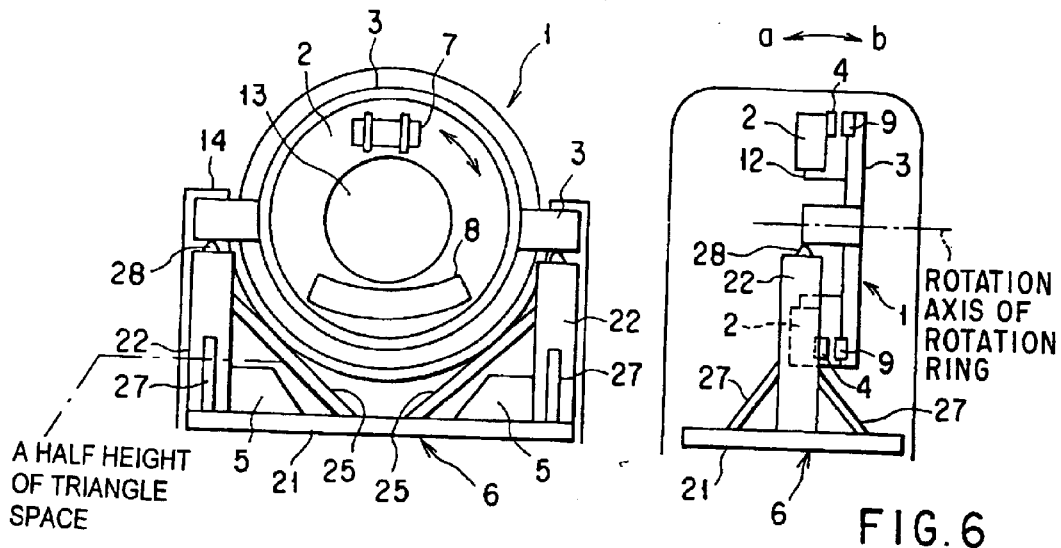
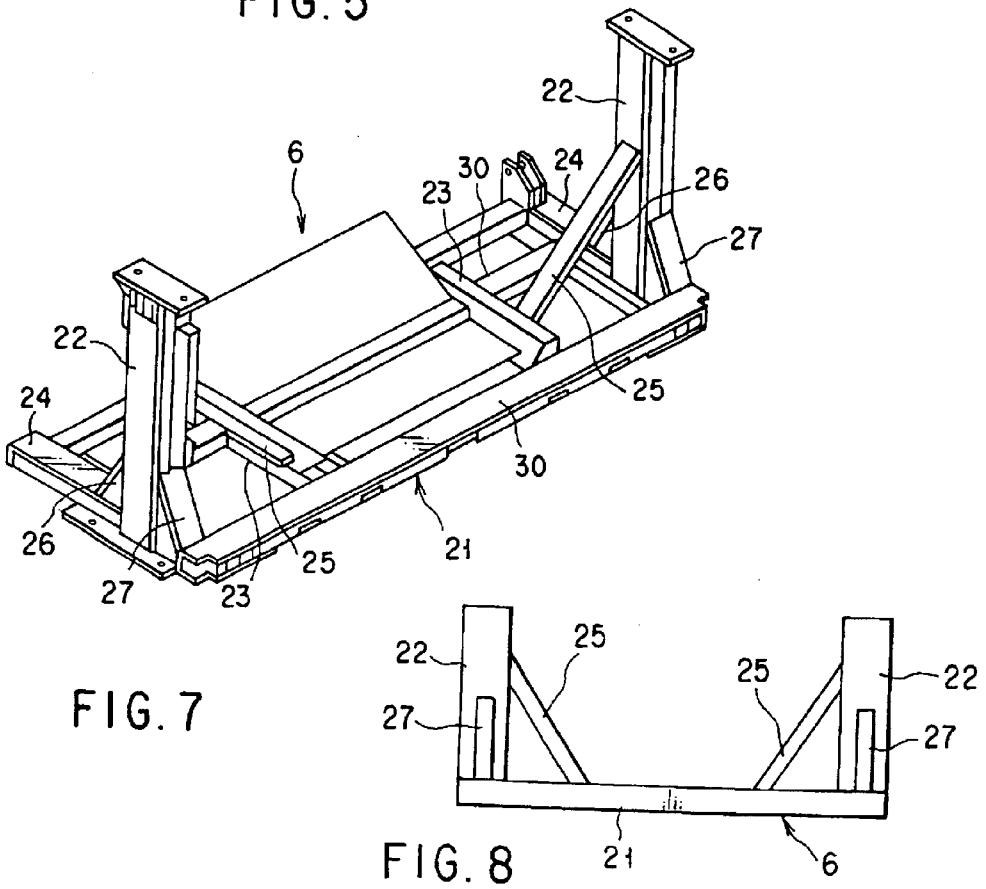

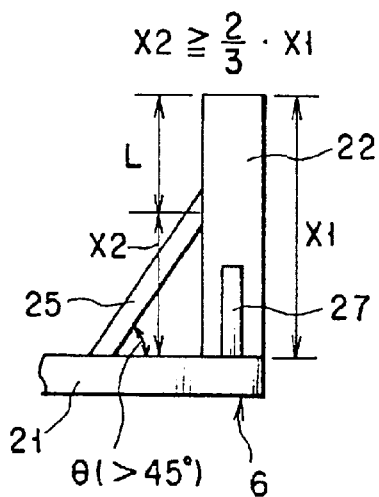
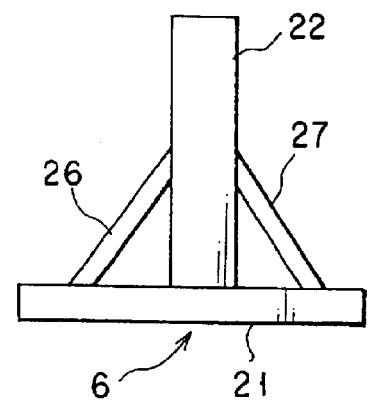
FIG. 9　　　　　FIG. 10
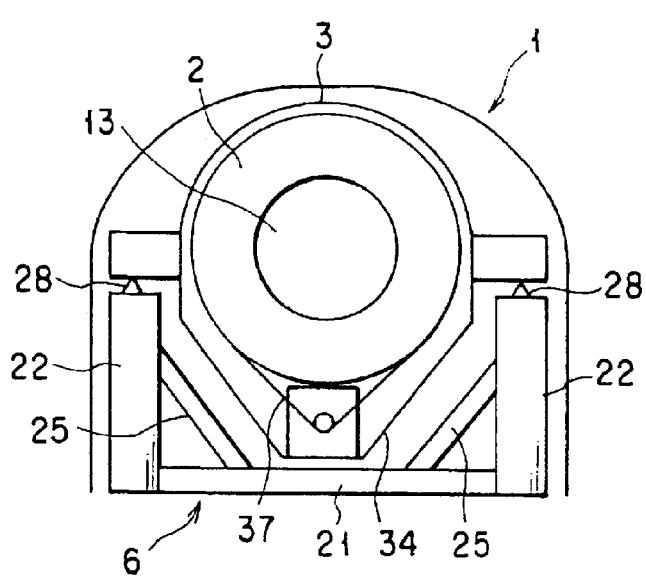
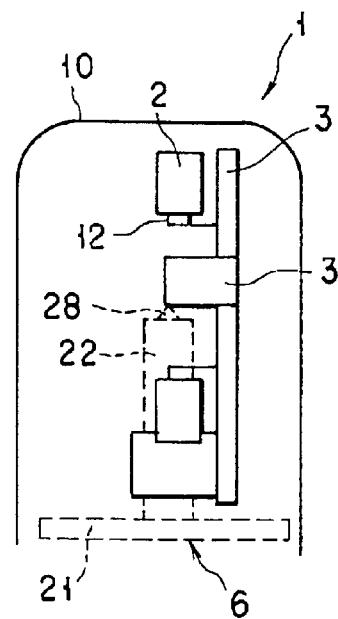
FIG. 11　　　　　FIG. 12

GANTRY OF AN X-RAY COMPUTER TOMOGRAPHY APPARATUS

BACKGROUND OF THE INVENTION

The present invention relates to a gantry for acquiring projection data, which is an important component of an X-ray computer tomography apparatus.

FIG. 1 shows external appearance of a conventional gantry. The gantry 100 has a box-like shape having a cylindrical hole (hereinafter referred to as a view field) 121 in the central portion thereof. A subject is inserted in the view field 121, when photographed. The cover 111 of the gantry 100 has an air intake 115 and an air outlet 116 to cool the interior of the gantry.

FIGS. 2 and 3 are front and side views of the interior of the gantry, respectively. The gantry has a rotation ring 101, on which an X-ray tube and an X-ray detector are mounted in an arrangement such that they are opposite to each other with the subject lying therebetween. The rotation ring 101 is rotatably supported by a ring frame 103. A motor 104 for rotating the rotation ring 101 is mounted on the ring frame 103. The ring frame 103 is supported by two main posts 106 via tilt mechanisms 110. The main post 106 is mounted on a stand base 107 at right angles, as shown in FIG. 4. The gantry 100 contains electric members 105, for example, a control board and a power source.

As well known, the standard scan time at present is a second for a rotation. In the near future, a direct drive system, which directly drives the rotation ring (rotor) 101 by a stator coil, will be the mainstream of the driver of a gantry.

Such high-speed rotations of the unbalanced rotation ring 101 cause the main posts 106 to vibrate violently. To suppress the vibration, the main posts 106 must be thick. For this reason, the gantry is inevitably large and heavy. Further, if the top end of the main post 106 is displaced 0.5 mm, a tumor or a bone smaller than 0.5 mm cannot be observed, and a ring-like artifact may be produced.

BRIEF SUMMARY OF THE INVENTION

An object of the present invention is to provide a gantry of a compact X-ray computer tomography apparatus having a high damping property.

A gantry of an X-ray computer tomography apparatus comprises a base, two main posts mounted on the base at right angles, a ring frame tiltably supported by the two main posts, a rotation ring rotatably supported by the ring frame, an X-ray tube mounted on the rotation ring, and an X-ray detector mounted on the rotation ring, opposing to the X-ray tube. The props obliquely abut on the main posts to reinforce them. Since the main posts are reinforced by the props, the vibration due to high-speed rotations of the rotation ring can be effectively suppressed. Moreover, since the main posts need not be thick, the gantry can be compact.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 5 is a front view showing the interior of a gantry of an X-ray computer tomography apparatus according to an embodiment of the present invention;

FIG. 6 is a side view showing the interior of the gantry shown in FIG. 5;

FIG. 7 is a perspective view of a stand shown in FIG. 5;

FIG. 8 is a front view of the stand shown in FIG. 5;

FIG. 9 is a front view showing details of props shown in FIG. 5;

FIG. 10 is a side view of the stand shown in FIG. 5;

FIG. 11 is a diagram showing a belt drive system to which the present invention is applied;

FIG. 12 is a side view showing the interior of the gantry shown in FIG. 11;

DETAILED DESCRIPTION OF THE INVENTION

Figure 1:
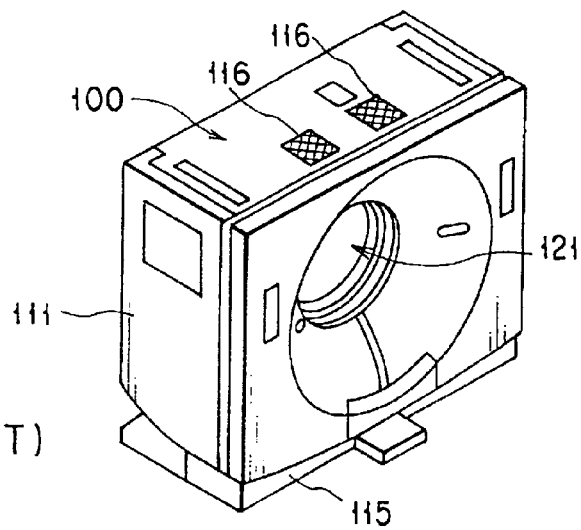
FIG. 1 is a diagram showing external appearance of a conventional X-ray computer tomography apparatus.
Figure 2:
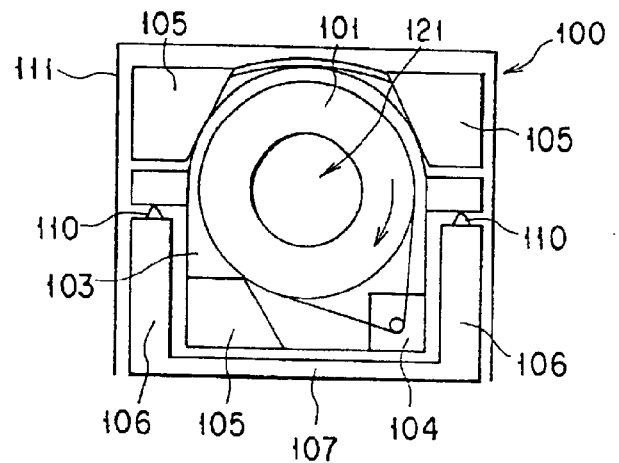
FIG. 2 is a front view showing the interior of a gantry shown in FIG. 1.
Figure 3:
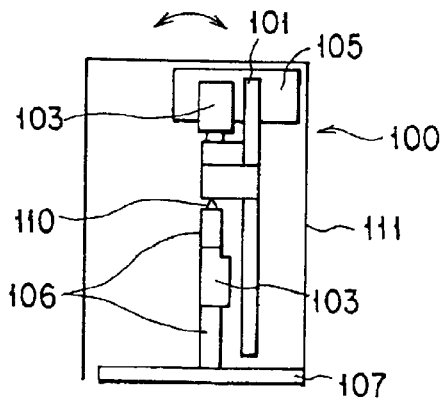
FIG. 3 is a side view showing the interior of the gantry shown in FIG. 1.
Figure 4:
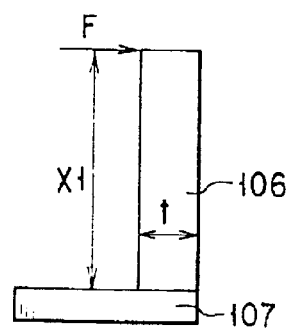
FIG. 4 is a side view showing a main post and a base shown in FIG. 2.

A preferred embodiment of a gantry of an x-ray computer tomography apparatus of the present invention will be described with reference to the accompanying drawings. As well known, the X-ray computer tomography apparatus acquires projection data on the subject in various angles, and reconstructs tomography image data by means of back projection or the like on the basis of the acquired projection date. The gantry is one of the most important components of the X-ray computer tomography apparatus for acquiring projection data.

As shown in FIGS. 5 and 6, the gantry comprises a rotatable portion 1 and a fixed portion (stand) 6 supporting the rotatable portion. The stand 6 includes a stand base 21 having two rectangular outside frames 24, two inside frames 30 for supporting the outside frames 24 and two cross bars 23 for reinforcing the inside frame 24. Two main posts 22 are mounted on the outside frame 24 of the stand base 21 at right angles. These members 21, 22, 23, 24 and 30 are covered with covers 14.

A disk-shaped ring frame 3 having a hole (view field) 13 in a central portion thereof is supported by two main posts 22 via tilt mechanisms 28. A disk-shaped rotation ring 2 is rotatably supported by the ring frame 3 via bearings 12. A subject is inserted in the hole 13, when photographed.

The rotation ring 2 is equipped with an X-ray tube 7 for generating X rays. Further, in the rotation ring 2, an X-ray detector 8 for detecting X rays transmitted through the subject is arranged so as to be opposite to the x-ray tube 7.

The gantry employs a direct motor drive system for directly rotating the rotation ring 2. Specifically, magnets 4 are attached to a peripheral portion of the rotation ring 2 at regular intervals, and stator coils 9 are attached to a peripheral portion of the ring frame 3 at regular intervals so as to face the magnets 4.

The direct motor drive system realizes high-speed rotations of the rotation ring 2. Since the rotation ring 2 is not completely balanced, the main posts 22 are vibrated by the high-speed rotations of the rotation ring 2. The vibration of the main post 22 is complicated: it is decomposed into a vibration component in a direction perpendicular to the rotation axis of the rotation ring 2 and a vibration component in a direction parallel to the rotation axis of the rotation ring 2. The former component is greater than the latter component.

To suppress the vibration component in the direction perpendicular to the rotation axis of the rotation ring 2, a prop 25, serving as a reinforce member of each main post 22, abuts on the main post 22 obliquely, across the main post 22 and the cross bar 23. Typically, one prop 25 is connected to each main post 22. The props 25 are arranged inside the two main posts 22, i.e., between the two main posts 22, to avoid an increase in size of the gantry.

In order to obtain a damping effect above a predetermined level, as well as to avoid an increase in size of the gantry, it is preferable that the upper end of the prop 25 be attached to a position at or above a height X2, ⅔ of the height X1 of the main post 22. At this time, the prop 25 is fixed to the base 21, at an angle of θ, greater than 45°, the reason for which will be described below.

The amount of displacement of the top end of the main post 22 can be expressed as $F \cdot L^3/(3 \cdot E \cdot I)$ based on a structural dynamics formula. F denotes a load (force) due to imbalance of the rotation ring 2, L denotes a length which receives the load F, E denotes a Young's modulus, and I denotes a geometrical moment of inertia of the main post 22. As clear from the above formula, the amount of displacement of the top end of the main post 22 is affected by the cube of the length L which receives the load F. Therefore, it is effective to shorten the length L which receives the load F by the prop 25, as shown in FIG. 9.

To only increase the damping effect, the props 25 may be connected to the top ends of the main posts 22. However, in this case, to prevent the props 25 from interfering with the rotation ring 2, it is necessary that the two main posts 22 be high and arranged at a long interval. As a result, the gantry inevitably becomes large. Therefore, to achieve the purposes of obtaining a damping effect above a predetermined level and avoiding an increase in size of the gantry, it is particularly preferable that the prop 25 support the main post 22 at a position at or above the height X2, two thirds of the height X1 of the main post 22. For reference, if the prop is not used, the thickness of the main post 22 must be 1.5 to 3 times that of the main post 22 reinforced by the prop 25 to obtain the same rigidity.

To suppress the vibration component in the direction parallel to the rotation axis of the rotation ring 2, two sub-props 26 and 27 are attached to each of the main post 22. The sub-props 26 and 27 abut on the main post 22 obliquely, across the main post 22 and the outside frame 24. The sub-props 26 and 27 are perpendicular to the prop 25. They are arranged at the angle of 180° around the main post 22. The sub-props 26 and 27 can be shorter than the prop 25, since the vibration component in the direction parallel to the rotation axis of the rotation ring 2 is smaller than that in the direction perpendicular to the rotation axis, and the two sub-props support the main post in the former direction.

Besides the above components, the gantry is equipped with various electric members 5, such as a power source unit for generating drive power to rotate the rotation ring 2 and tilt the ring frame 3, a scan control unit for controlling a rotating operation of the rotation ring 2 and a detecting operation of the X-ray detector 8, and a transmission unit for externally outputting a signal detected by the X-ray detector 8. All the electric members 5 can be received in two triangle spaces defined by the base 21, the main posts 22 and the props 25. Thus, the gantry can be compact, and moreover stable since it has a low center of gravity. The power source unit (strong electric system), the scan control unit and the transmission unit (weak electric system) may be received in one triangle space.

As described above, according to the present invention, since the main posts 22 are reinforced by the props 25, 26 and 27, the vibration generated by the high-speed rotations of the rotation ring 2 can be effectively suppressed without thickening the main posts 22. In addition, since all electric members are stored in the spaces defined by the base 21, the main posts 22 and the props 25, the gantry can be compact and high stability can be obtained.

The above embodiment can be modified variously. According to the above description, the rotation ring 2 is rotated by the direct motor drive system; however, as shown in FIGS. 11 and 12, it can be rotated by a belt drive system using a motor 34 and a belt 37. In this modification, the motor 34 is located immediately under the rotation ring 2 to secure the space where props 25 are fixed.

Figure 13:
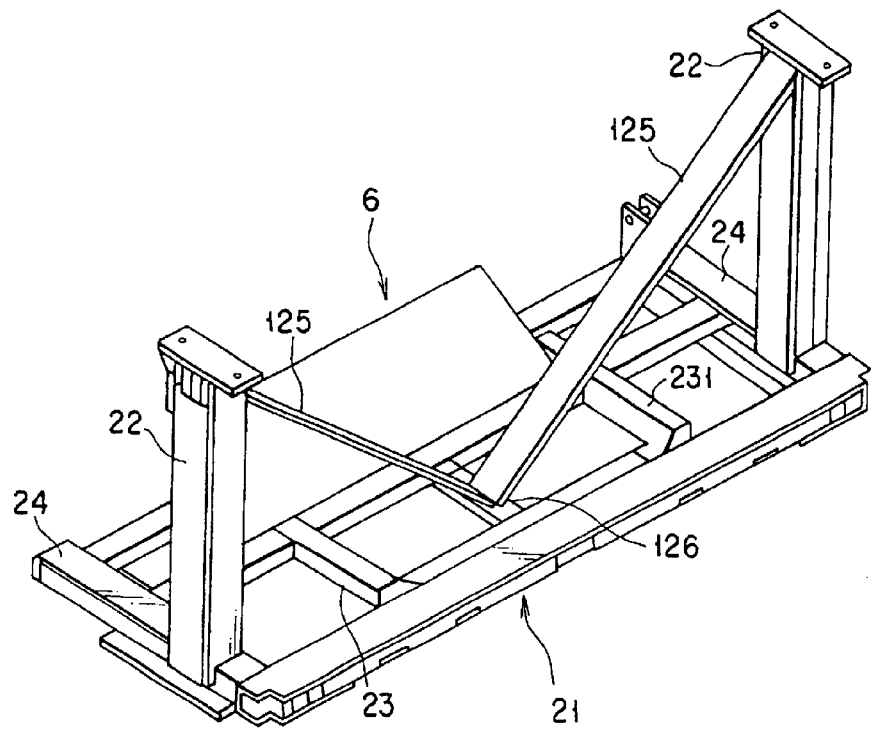
FIG. 13 is a diagram showing a modification of the stand according to the embodiment of the present invention.

Further, as shown in FIG. 13, a prop 125 can be connected across the top end of each main post 22 and a cross bar 126 provided substantially at the center of the base 21, so that the damping effect can be further improved. However, in this case, the main posts 22 must be high and spaced at a relatively long distance in order to prevent the props 125 from interfering with the rotation ring 2. As a result, the gantry must be somewhat large in size.

Figure 14:
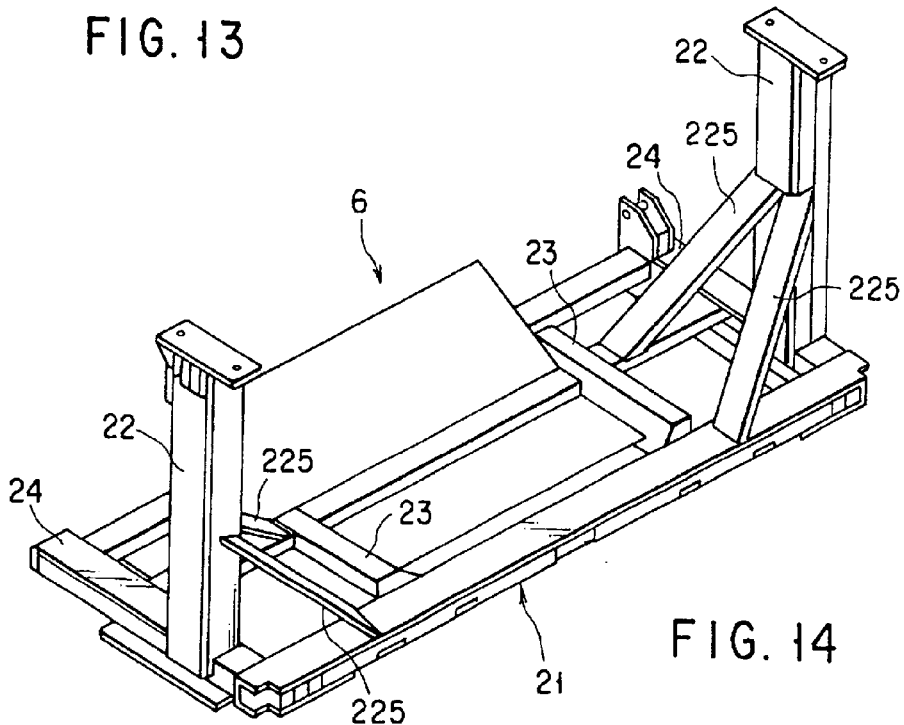
FIG. 14 is a diagram showing another modification of the stand according to the embodiment of the present invention.

Furthermore, as shown in FIG. 14, two props may be provided for each of the two main posts. In this case, the two props 225 are arranged to form an inverted V shape inward from the main post 22. Moreover, the vibration components in a plurality of directions can be effectively suppressed by an arrangement in which the two props 225 form an angle of 90° around the main post 22.

Figure 15:
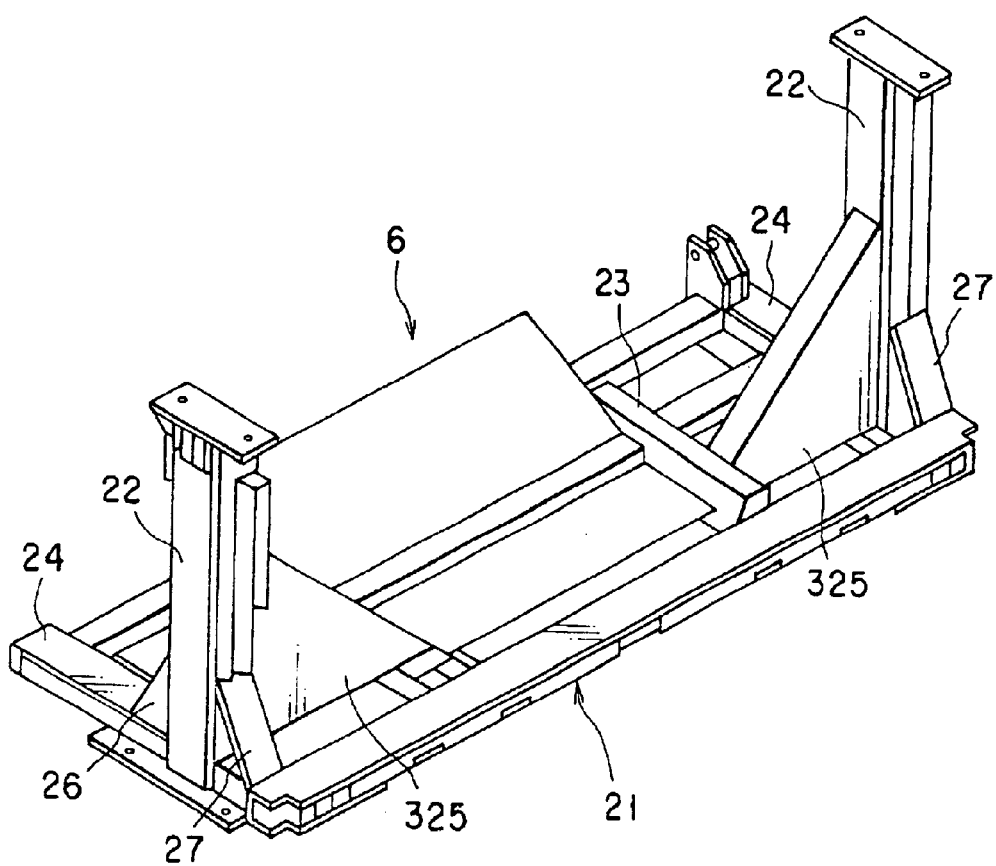
FIG. 15 is a diagram showing still another modification of the stand according to the embodiment of the present invention.

Further, the reinforce member of the main post 22 is not limited to a prop, but may be a triangular block 325 as shown in FIG. 15.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A gantry of an X-ray computer tomography apparatus comprising:
   an X-ray tube;
   an X-ray detector;
   a rotation ring mounting said X-ray tube and said X-ray detector;

a ring frame rotatably supporting said rotation ring;

a base;

a plurality of main posts vertically mounted on said base and supporting said ring frame such that said rotation ring is positioned between said main posts;

a plurality of props extending obliquely between said main posts for reinforcing said main posts under the rotation ring; and at least one electric member positioned in at least one of spaces surrounded by said base, main posts and props such that the at least one electric member is disposed in a lower half portion of a respective one of the spaces, said at least one electric member including at least one of a power source unit configured to generate driver power to rotate said rotation ring and tilt said ring frame, a scan control unit configured to control a rotating operation of said rotation ring and a detecting operation of said X-ray detector, and a transmission unit configured to externally output a signal detected by said X-ray detector.

2. A gantry according to claim 1, wherein the props are arranged between the two main posts.

3. A gantry according to claim 2, wherein the base comprises outside frames, inside frames and cross bars provided inside the frame, the props being connected between the cross bars and the main posts.

4. A gantry according to claim 1, wherein each of the main posts is provided with one prop.

5. A gantry according to claim 4, wherein the props are mounted on a central portion of the base.

6. A gantry according to claim 1, wherein each of the main posts is provided with two props.

7. A gantry according to claim 6, wherein the two props are arranged to form an inverted V shape inward from the main post.

8. A gantry according to claim 7, wherein the two props form an angle of 90° around the main post.

9. A gantry according to claim 1, wherein each of the props abuts on the main post at a height at least two thirds of the main post.

10. A gantry according to claim 1, wherein each of the props is fixed to the base at an angle of at least 45°.

11. A gantry according to claim 1, further comprising sub-props abutting on the main posts obliquely, the sub-props being perpendicular to the props.

12. A gantry according to claim 11, wherein the sub-props are shorter than the props.

13. A gantry according to claim 11, wherein each of the main posts is provided with two sub-props.

14. A gantry according to claim 13, wherein the two sub-props are arranged at an angle of 180° around the main post.

15. A gantry according to claim 1, wherein said at least one electric member comprises a plurality of electric members including said power source unit, said scan control unit, and said transmission unit.

16. A gantry of an X-ray computer tomography apparatus comprising:

an X-ray tube;

an X-ray detector;

a rotation ring mounting said X-ray tube and said X-ray detector;

a ring frame rotatably supporting said rotation ring;

a base;

a plurality of main posts vertically mounted on said base and supporting said ring frame such that said rotation ring is positioned between said main posts;

a plurality of reinforce members positioned between said main posts for reinforcing said main posts under the rotation ring; and at least one electric member positioned in at least one of spaces surrounded by said base, main posts and reinforce members such that the at least one electric member is disposed in a lower half portion of a respective one of the spaces, said at least one electric member including at least one of a power source unit configured to generate driver power to rotate said rotation ring and tilt said ring frame, a scan control unit configured to control a rotating operation of said rotation ring and a detecting operation of said X-ray detector, and a transmission unit configured to externally output a signal detected by said X-ray detector.

* * * * *